United States Patent [19]

Tokarzewski et al.

[11] Patent Number: 4,533,492
[45] Date of Patent: Aug. 6, 1985

[54] ACETYL DIMETHYLBUTYLCYCLOHEXENE AND ORGANOLEPTIC USES THEREOF

[75] Inventors: Richard J. Tokarzewski, Atlantic Highlands; William L. Schreiber, Jackson, both of N.J.

[73] Assignee: International Flavors & Fragrances Inc., New York, N.Y.

[21] Appl. No.: 578,626

[22] Filed: Feb. 9, 1984

Related U.S. Application Data

[62] Division of Ser. No. 482,824, Apr. 7, 1983, Pat. No. 4,449,009.

[51] Int. Cl.³ ............................................. C11B 9/00
[52] U.S. Cl. ............................. 252/522 R; 131/276; 252/8.6; 252/174.11; 252/187.24; 252/522 A; 514/690; 514/844
[58] Field of Search ............... 252/8.6, 174.11, 522 R, 252/522 A, 187.24; 131/276; 424/69

[56] References Cited

U.S. PATENT DOCUMENTS 3,929,895 12/1975 Hall ............................ 252/522 R X
4,360,032 11/1983 Trenkle et al. ..................... 131/276

FOREIGN PATENT DOCUMENTS 2005671 4/1979 United Kingdom ............ 252/522 R

OTHER PUBLICATIONS

Arctander, *Perfume and Flavor Chemicals,* vols. I and II, Monographs 378, 2212, 2252, and 2321, (1967).

*Primary Examiner*—Thomas A. Waltz
*Attorney, Agent, or Firm*—Arthur L. Liberman

[57] ABSTRACT

Described is the compound defined according to the structure:

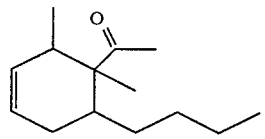

and the uses thereof in augmenting or enhancing the aroma or taste of perfume compositions, perfumed articles, colognes, smoking tobacco or smoking tobacco articles.

7 Claims, 5 Drawing Figures

FIG. 2
GLC PROFILE FOR FRACTION 6 OF EXAMPLE I.

FIG. 1
GLC PROFILE FOR EXAMPLE I. CRUDE

FIG.3

GLC PROFILE FOR FRACTION 7 OF EXAMPLE I.

FIG. 5

IR SPECTRUM FOR FRACTION 6 OF EXAMPLE I.

ACETYL DIMETHYLBUTYLCYCLOHEXENE AND ORGANOLEPTIC USES THEREOF

This is a divisional of application Ser. No. 482,824, filed 4/7/83, now U.S. Pat. No. 4,449,009.

BACKGROUND OF THE INVENTION

The present invention provides acetyl dimethylbutylcyclohexene compounds defined according to the structure:

and uses thereof in augmenting or enhancing the aroma or taste of consumable materials including smoking tobacco compositions, smoking tobacco articles, perfume compositions, perfumed articles and colognes.

In the perfumery art there is a considerable need for constituents having green, violet, floral, woody, peppery, and amber aroma profiles. Fruity, hay-like and woody aromas and tastes both prior to and on smoking in the main stream and in the side stream are desirable in smoking tobacco, flavoring compositions and substitutes smoking tobacco flavoring compositions.

Specifically described herein are materials having such organoleptic profiles but which do not discolor with age. Such materials have a wide utilization in the presence of perfume compounds and in tobacco flavoring compounds. A limited amount of such materials that give rise to one or more of these properties individually is available from natural sources, but the natural materials are subject to wide variations in quality, are expensive and are often in critically short supply.

The instant invention provides the foregoing which the prior art has heretofore failed to provide. Furthermore, nothing in the prior art shows the unexpected, unobvious and advantageous value of carrying out a process of augmenting or enhancing the aroma or taste of consumable materials including perfume compositions, perfumed articles and colognes, as well as smoking tobaccos and smoking tobacco compositions using the compound defined according to the structure:

Described in the prior art are compounds defined according to the structure:

(U.S. Pat. No. 4,360,032) as well as the structures:

("Perfume & Flavor Chemicals") (Aroma Chemicals), Volumes I, II by Steffen Arctander, 1969, Monograph 2212 and compounds having the structure:

(Arctander, Vol. II, Monograph 2252) and having the structure:

(Arctander, Vol. II, Monograph 2321).

U.S. Pat. No. 4,360,032 indicates that the compounds defined according to the structure:

rounds out raspberry flavors and has a very useful grape juice nuance. Arctander, at Monograph 2212 indicates that the chemical having the structure:

has a sweet, fruity-woody odor of moderate to good tenacity. Arctander at Monograph 2252, indicates that the compound having the structure:

has a sweet-camphoraceous, rosy-citrusy odor of moderate tenacity. Arctander at Monograph 2321, indicates that the compound having the structure:

has a warm and bitter-sweet, green-floral, woody-leafy odor of moderate tenacity having warm and honey-like undertones.

None of the compounds of the prior art however have the unexpected, unobvious and advantageous organoleptic properties of the compound defined according to the structure:

or its isomers such as that having the structure:

Nothing in the prior art sets forth the synthesis of the compound defined according to the structure:

according to the reaction:

to produce a compound having from a perfumery standpoint a green, violet, floral, woody, peppery and amber aroma profile and a fruity, hay-like and woody aroma and taste tobacco flavor profile both prior to and on smoking in both the main stream and the side streams.

BRIEF DESCRIPTION OF THE DRAWINGS

(Conditions: Carbowax column programmed at 100°–220° C. at 8° C. per minute.)

(Conditions: Carbowax column programmed at 100°–220° C. at 8° per minute.)

(Conditions: Carbowax column programmed at 100°–220° C. at 8° C. per minute.)

(Conditions: Field strength 100 MHz, solvent CFCl$_3$.)

THE INVENTION

It has now been determined that acetyl dimethylbutylcyclohexene derivatives defined according to the structure:

which include various optical and cis and trans isomers including that having the structure:

are capable of imparting, augmenting or enhancing a variety of fragrances, aromas and tastes in or to consumable materials.

Briefly our invention contemplates, augmenting or enhancing fragrances of such consumable materials as perfumes, perfumed articles (e.g., solid or liquid anionic, cationic, nonionic or zwitterionic detergents, cosmetic powders, fabric softener compositions, drier-added fabric softener articles perfumed hypochlorite bleaches and perfume polymers) and colognes by adding thereto a small but effective amount of at least one of the isomers defined according to the structure:

Furthermore, our invention contemplates, augmenting or enhancing the aroma or taste of smoking tobacco compositions and smoking tobacco articles including tobacco bodies of cigarettes, the wrapper and the filter of cigarettes and cigars by adding to one or more parts of such smoking tobacco articles or by adding to smoking tobacco compositions an aroma or taste augmenting, enhancing or modifying quantity of at least one of the isomers defined according to the structure:

including the isomer having the structure:

The compounds of our invention defined according to the structure:

may be prepared by reacting piperylene having the structure:

with 3-methyl-octene-3-one-2 defined according to the structure:

by means of a Diels-alder reaction thusly:

The Diels-alder reaction may be carried out according to the conditions of Ayyar, Cookson and Kagi, J.Chem.Soc., Perkin Trans. 1, 1975 (17) 1724–36 [Title: "Synthesis of Delta-Damascone [trans-1-(2,6,6-trimethylcyclohex-3-enyl)but-2-enlone]and Beta-Damascenone [trans-1-(2,6,6-trimethylcyclohexa-1,3-dienyl)but-2-en-1-one]"]. The reaction may take place in the presence of a catalyst such as a Lewis acid catalyst such as aluminum trichloride, titanium tetrachloride or stanic chloride at lower temperatures, e.g., 0°–50° C. or in the absence of a catalyst at higher temperatures, e.g., 40°-100° C.

More specifically, the ratio of diene:ketone may be in the range of from about 1:1 (mole ratio) up to about 10:1 with a mole ratio of diene:ketone preferably being about 1.5:1. The reaction may be carried out as stated, supra, in the presence of a Lewis acid catalyst such as aluminum trichloride zinc chloride, titanium tetrachloride, borontrifluoride point etherate, ethyl aluminum dichloride, diethyl aluminum chloride and other Lewis acid catalysts. The reaction may be carried out in the presence of or in the absence of a solvent. When using a solvent, solvents such as toluene, xylene and chlorinated solvents may be used which are inert to the reactants at the conditions of the reaction.

The reaction may be carried out in the absence of such a Lewis acid catalyst at higher temperatures. Accordingly, the reaction may be carried out at temperatures of between −15° C. and 100° C. preferably in the presence of a catalyst at a temperature of from −10° C. up to about 50° C. The reaction may be carried out at atmospheric pressure, super atmospheric pressure, and sub-atmospheric pressures. Most conveniently and economically and preferably the reaction is carried out at atmospheric pressure. When not using a catalyst, the reaction may be carried out at temperatures of from about 40° C. up to about 100° C.

The resulting product of the reaction may be "worked up" according to standard extraction and distillation procedures and the isomers (e.g., the cis and trans isomers and the optical isomers) may be used in admixture "as is" or they may be separated by standard techniques in order to form sterio isomers and "cis" and "trans" isomers including such isomers as that having the structure:

The resulting product defined according to the structure:

from a perfumery standpoint has a green, violet, floral, woody, peppery and amber aroma profile. From a smoking tobacco organoleptic standpoint, it has a fruity, hay-like and woody aroma and taste profile both prior to and on smoking in the main stream and the side stream.

The acetyl dimethylbutylcyclohexene and organoleptic uses thereof and one or more axilliary perfume ingredients including, for example, alcohols, aldehydes, ketones other than the acetyl dimethylbutylcyclohexene and the organoleptic uses thereof of our invention, hydrocarbons including terpinic hydrocarbons, nitriles, esters, lactones, natural essential oils and synthetic essential oils may be admixed so that the combined odors of the individual components produce a pleasant and desired fragrance, particularly and preferably in patchouli fragrances. Such perfume compositions usually contain (a) the main note or "bouquet" or foundation stone of the composition; (b) modifiers which round off and accompany the main note; (c) fixatives which include odorous substances which lend a particular note to the perfume throughout all stages of evaporation and substances which retard evaporation; and (d) top-notes which are usually low boiling fresh smelling materials.

In perfume compositions, it is the individual components which contribute to their particular olfactory characteristics, however the overall sensory effect of the perfume composition will be at least the sum total of the effects of each of the ingredients. Thus, the acetyl dimethylbutylcyclohexenes of our invention can be used to alter, modify or enhance the aroma characteristics of a perfume composition, for example, by utilizing or moderating the olfactory reaction contributed by another ingredient in the composition.

The amount of the acetyl dimethylbutylcyclohexenes of our invention which will be effective in perfume compositions as well as in perfumed articles and colognes depends on many factors, including the other ingredients, their amounts and the effects which are desired. It has been found that perfume compositions containing as little as 0.01% of the compound defined according to the structure:

or even less (e.g., 0.005%) can be used to impart a green, violet, floral, woody, peppery and amber aroma profile to soaps, anionic, cationic and nonionic detergents, fabric softener articles (such as BOUNCE ®, a registered trademark of the Procter & Gamble Company of Cincinnati, Ohio), cosmetics or other products. The amount employed can range up to 70% of the fragrance components and will depend on considerations of cost, nature of the end product, the effect desired on the finished product and the particular fragrance sought.

The acetyl dimethylbutylcyclohexene and organoleptic uses thereof of our invention are useful (taken alone or together with other ingredients in perfume compositions) as (an) olfactory component(s) in solid and liquid anionic, cationic and nonionic detergents and soaps, space odorants and deodorants, perfumes, colognes, toilet water, bath preparations, such as creams, deodorants, hand lotions, and sunscreens; powders, such as talcs, dusting powders, face powders, perfume polymers which include perfume polyethylene and polypropylene and perfume nylon. When used as olfactory components as little as 0.1% of the acetyl dimethylbutylcyclohexenes of our invention will suffice to impart an intense green, violet, floral, woody, peppery, and amber aroma profile to patchouli formulations. Generally, nor more than 5% of the acetyl dimethylbutylcyclohexenes of our invention based on the ultimate end product, is required in the perfume composition.

In addition, the perfume compositions or fragrance compositions of our invention can contain a vehicle, or carrier for the acetyl dimethylbutylcyclohexenes of our invention. The vehicle can be a liquid such as an alcohol, e.g., ethanol, a non-toxic glycol, such as propylene glycol or the like. The carrier can also be an absorbent solid, such as a gum (e.g., gum arabic, xanthan gum or guar gum) or components for encapsulating the composition (such as gelatin), for example, by means of coacervation or, for example, a urea-formaldehyde polymer.

The range of use of the acetyl dimethylbutylcyclohexenes of our invention in perfumed articles can vary from 0.1% up to about 5%.

It will thus be apparent that the acetyl dimethylbutylcyclohexenes of our invention can be utilized to alter, modify or enhance sensory properties, particularly organoleptic properties, in a wide variety of consumable materials.

Furthermore, the acetyl dimethylbutylcyclohexenes of our invention are capable of supplying and/or potentiating certain flavor and aroma notes usually lacking in many tobacco flavors heretofore provided.

As used herein in regard to tobacco flavors, the terms "alter" and "modify" in their various forms means "supplying or imparting flavor character or note to otherwise bland tobacco, tobacco substitutes, or tobacco flavor formulations or augmenting the existing flavor characteristic where a natural flavor is deficient in some regard or supplementing the existing flavor impression to modify its quality, character or taste".

As used herein, the term "enhance" is intended to mean the intensification (without change in kind of quality of aroma or taste) of one or more taste and/or aroma nuances present in the organoleptic impression of a tobacco or a tobacco substitute or a tobacco flavor.

Our invention thus provides an organoleptically improved smoking tobacco product and additives therefor, as well as methods of making the same which overcome specific problems heretofore encountered in which specific desired fruity, hay-like and woody aroma and taste nuances are created or enhanced and may be readily controlled and maintained at the desired uniform level regardless of variations in the smoking tobacco components of the blend.

This invention further provides improved tobacco additives and methods whereby various fruity, hay-like and woody notes may be imparted to smoking tobacco products and may be readily varied and controlled to produce the desired uniform flavor characteristics.

In carrying out this aspect of our invention, we add to smoking tobacco materials or a suitable substitute therefor (e.g., dried lettuce leaves) an aroma and flavor additive containing as an active ingredient the compound defined according to the structure:

or one or more individual isomers thereof, for example, that having the structure:

In addition to the acetyl dimethylbutylcyclohexenes of our invention, other flavoring and aroma additives may be added to the smoking tobacco materials or substitute therefor either separately or in admixture with the acetyl dimethylbutylcyclohexenes of our invention as follows:

(i) Synthetic Materials

Beta-ethyl-cinnamaldehyde;
Beta-cyclohomocitral;
Eugenol;
Dipentene;
Beta-damascenone;
Alpha-damascone;
Beta-damascone;
Cis,trans-alpha-damascone;
Maltol;
Ethyl Maltol;
Delta-undecalactone;
Delta-decalactone;
Benzaldehyde;
Amyl acetate;
Ethyl butyrate;
Ethyl valerate;
Ethyl acetate;
2-Hexenol-1;
2-Methyl-5-isopropyl-1,3-nonadiene-8-one;
2,6-Dimethyl-2,6-undecadiene-10-one;
2-Methyl-5-isopropyl acetophenone;
2-Hydroxy-2,5,5,8a-tetramethyl-1-(2-hydroxyethyl)-decahydronaphthalane;
Dodecahydro-3a,6,6,9a-tetramethylnaphtho[2,1,b]furan;
4-Hydroxy hexanoic acid, gamma lactone; and
Polyisoprenoid hydrocarbons defined in Example V of U.S. Pat. No. 3,589,372 issued on June 29, 1971.

(ii) Natural Oils

Celery seed oil;
Coffee extract;
Bergamot Oil;
Cocoa extract;
Nutmeg Oil;
Origanum Oil.

An aroma and flavoring concentrate containing one or more of the acetyl dimethylbutylcyclohexenes of our invention, and if desired, one or more of the above-indicated additional flavoring additives amy be added to the smoking tobacco material, to the filter or to the leaf or paper wrapper. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste but insofar as enhancement or the imparting of natural and/or fruity, hay-like or woody notes, we have found that satisfactory results are obtained if the proportion by weight of the sum total of the acetyl dimethylbutylcyclohexenes of our invention to smoking tobacco material is between 250 ppm and 1,500 ppm (0.25–0.15%) of the active ingredients to the smoking tobacco material. We have further found that satisfactory results are obtained if the proportion by weight of the sum total of the compound defined according to the structure:

used to flavoring material is between 2,500 and 15,000 ppm (0.25%–1.5%).

Any convenient method for incorporating the acetyl dimethylbutylcyclohexenes in the smoking tobacco product may be employed. Thus, the acetyl dimethylbutylcyclohexene of our invention taken alone or taken further together with other flavoring additives as set forth above, may be applied by means of a suitable applicator such as a brush or roller on the paper or leaf wrapper for the smoking product, or it may be applied to the filter by either spraying, dipping or coating.

Furthermore, it will be apparent that only a portion of the tobacco or substitute thereof need be treated and the thus treated tobacco may be blended with other tobaccos before the ultimate tobacco product is formed. In such cases, the tobacco treated may have the acetyl dimethylbutylcyclohexenes of our invention in excess of the amounts or concentrations above-indicated so that when blended with other tobaccos, the final product will have the percentage within the indicated range.

In accordance with one specific example of our invention, an aged, cured and shredded domestic burley tobacco is sprayed with a 20% ethyl alcohol solution of the compound having the structure:

prepared according to Example I, infra, in an amount to provide a tobacco composition containing 200 ppm by weight of the compound defined according to the structure:

Thereafter, the alcohol is removed by evaporation and the tobacco is manufactured into cigarettes by means of the usual techniques. The cigarette when treated as indicated has a desired and pleasing aroma (increased smoke body sensation in the mouth with enhanced tobacco-like notes and pleasant aromatic nuances) which is detectable in the main and sidestreams when the cigarette is smoked. This aroma is described as having a fruity, hay-like and woody aroma with sweet, floral and fruity undertones prior to and on smoking both in the mainstream and the sidestream.

While our invention is particularly useful in the manufacture of smoking tobacco, such as cigarette tobacco, cigar tobacco and pipe tobacco, other tobacco products formed from sheeted tobacco dust or fines may also be used. Likewise, the acetyl dimethylbutylcyclohexenes of our invention can be incorporated with materials such as filter tip materials, seam paste, packaging materials and the like which are used along with smoking tobacco to form a product adapted for smoking. Furthermore, the acetyl dimethylbutylcyclohexenes of our invention can be added to certain smoking tobacco substitutes of natural or synthetic origin (e.g., dried lettuce leaves) and, accordingly, by the term "tobacco" as used throughout this specification is meant any composition intended for human consumption by smoking, whether composed of tobacco plant parts or substitute materials or both.

The following examples serve to illustrate our invention. However, our invention is not intended to be limited thereto but is only intended to be limited insofar as the claims are concerned. All parts and percentages given herein are by weight unless otherwise specified.

EXAMPLE I

Preparation of Acetyl Dimethylbutylcyclohexene

Reaction:

Into a 1-liter flask equipped with stirrer, thermometer, and reflux condenser is added a mixture of 150 ml anhydrous toluene and 13.4 grams of aluminum chloride. While maintaining the reaction temperature at 10° C. over a period of 10 minutes, 128 grams (0.91 moles) of 3-methyl-oct-3-ene-2-one is added to the reaction mass. Over a period of 1 hour, 250 grams (1.47 moles) of a 40% solution of piperylene in toluene is added to the reaction mass while maintaining the reaction mass at 10° C. The reaction mass is stirred at a temperature of about 10° C. for a period of 2 hours. The reaction mass is then distilled on a spinning band column yielding the following fractions:

| Fraction No. | Liquid Temp. (°C.) | Vapor Temp. (°C.) | Vacuum mm/Hg. Pressure |
|---|---|---|---|
| 1 | 116 | 60 | 2.0 |
| 2 | 102 | 74 | 2.0 |
| 3 | 116 | 80 | 2.0 |
| 4 | 116 | 82 | 2.0 |
| 5 | 116 | 86 | 2.0 |
| 6 | 118 | 86 | 2.0 |

| Fraction No. | Liquid Temp. (°C.) | Vapor Temp. (°C.) | Vacuum mm/Hg. Pressure |
|---|---|---|---|
| 7 | 126 | 90 | 2.3 |
| 8 | 162 | 90 | 2.4 |
| 9 | 200 | 72 | 2.5 |

The reflux ratio for the spinning band column is 4:1.

Figure 1:
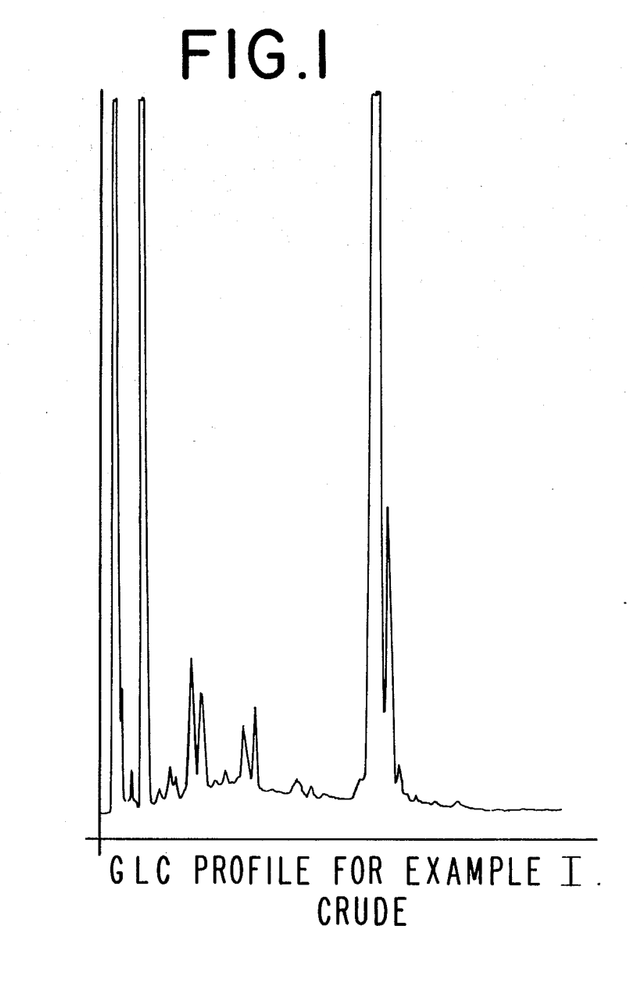
FIG. 1 is a GLC profile of the crude reaction product produced according to Example I containing the compound having the structure.

FIG. 1 is the GLC profile for the crude reaction product prior to distillation. (Conditions: Carbowax column programmed at 100°–220° C. at 8° C. per minute.)

Figure 2:
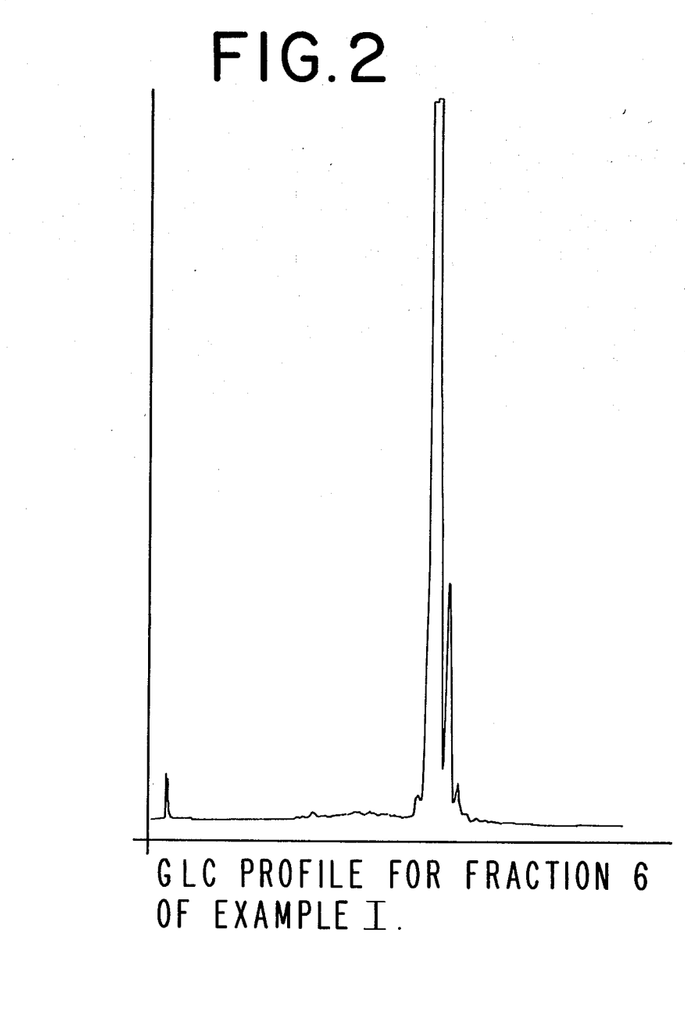
FIG. 2 is the GLC profile for Fraction 6 of the distillation product of the reaction product of Example I containing the compound having the structure.

FIG. 2 is the GLC profile for Fraction 6 of the foregoing distillation.

Figure 3:
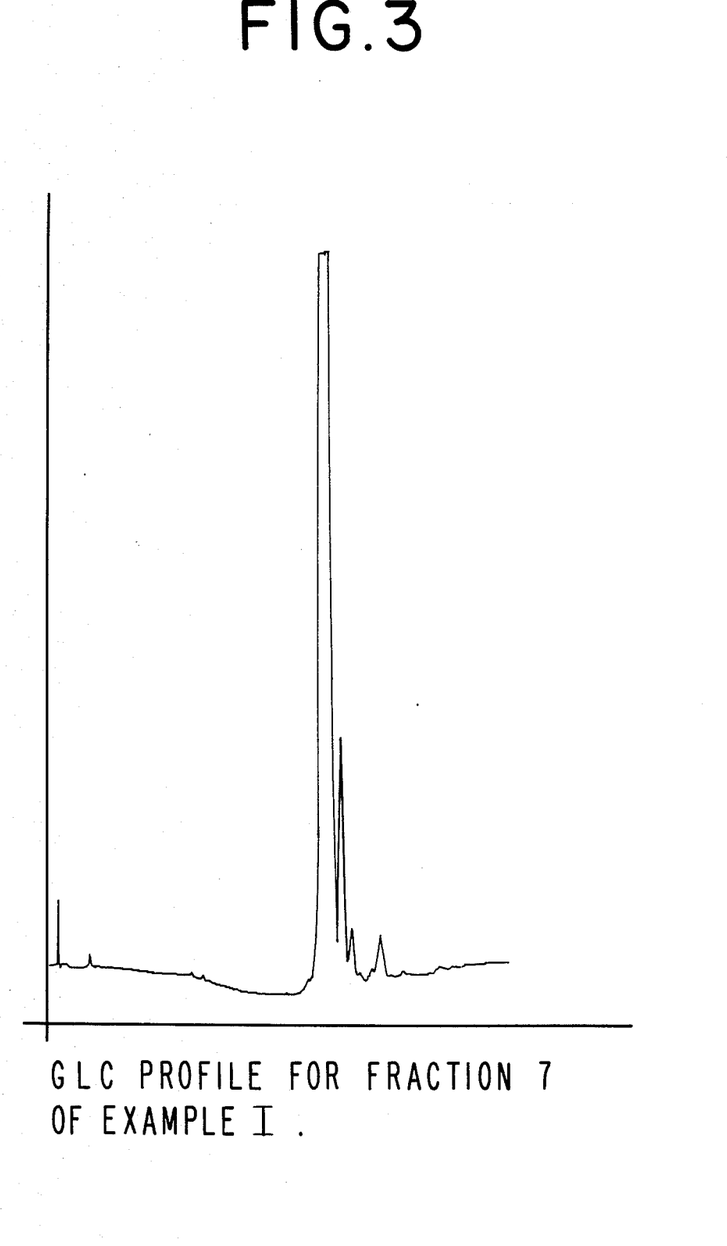
FIG. 3 is the GLC profile for Fraction 7 of the distillation product of the reaction product of Example I containing the compound having the structure.

FIG. 3 is the GLC profile for Fraction 7 of the foregoing distillation.

Figure 4:
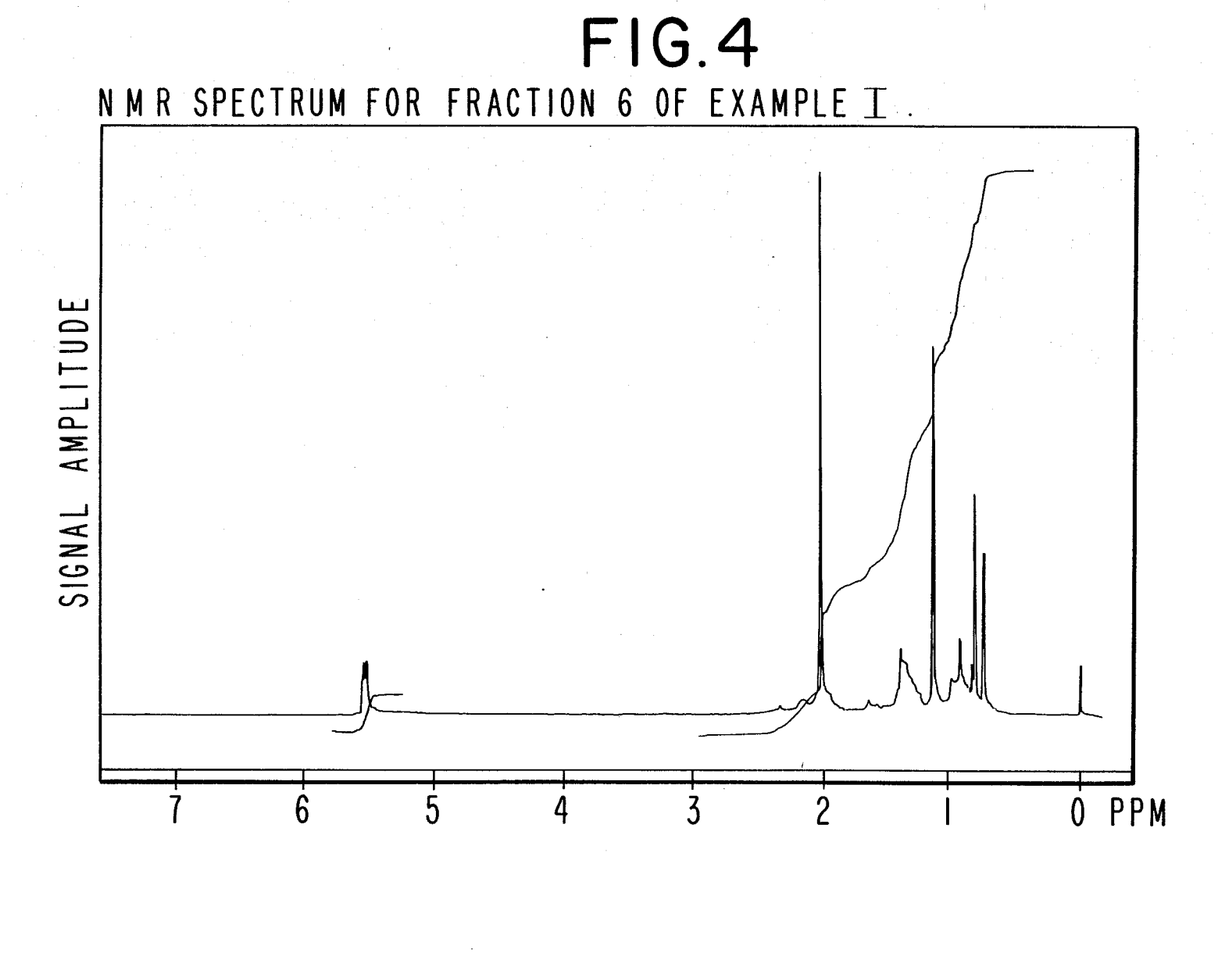
FIG. 4 is the NMR spectrum for Fraction 6 of the distillation product of the reaction product of Example I containing the compound having the structure.

FIG. 4 is the NMR spectrum for Fraction 6 of the foregoing distillation. (Conditions: 100 MHz field strength; $CFCl_2$ solvent.)

Figure 5:
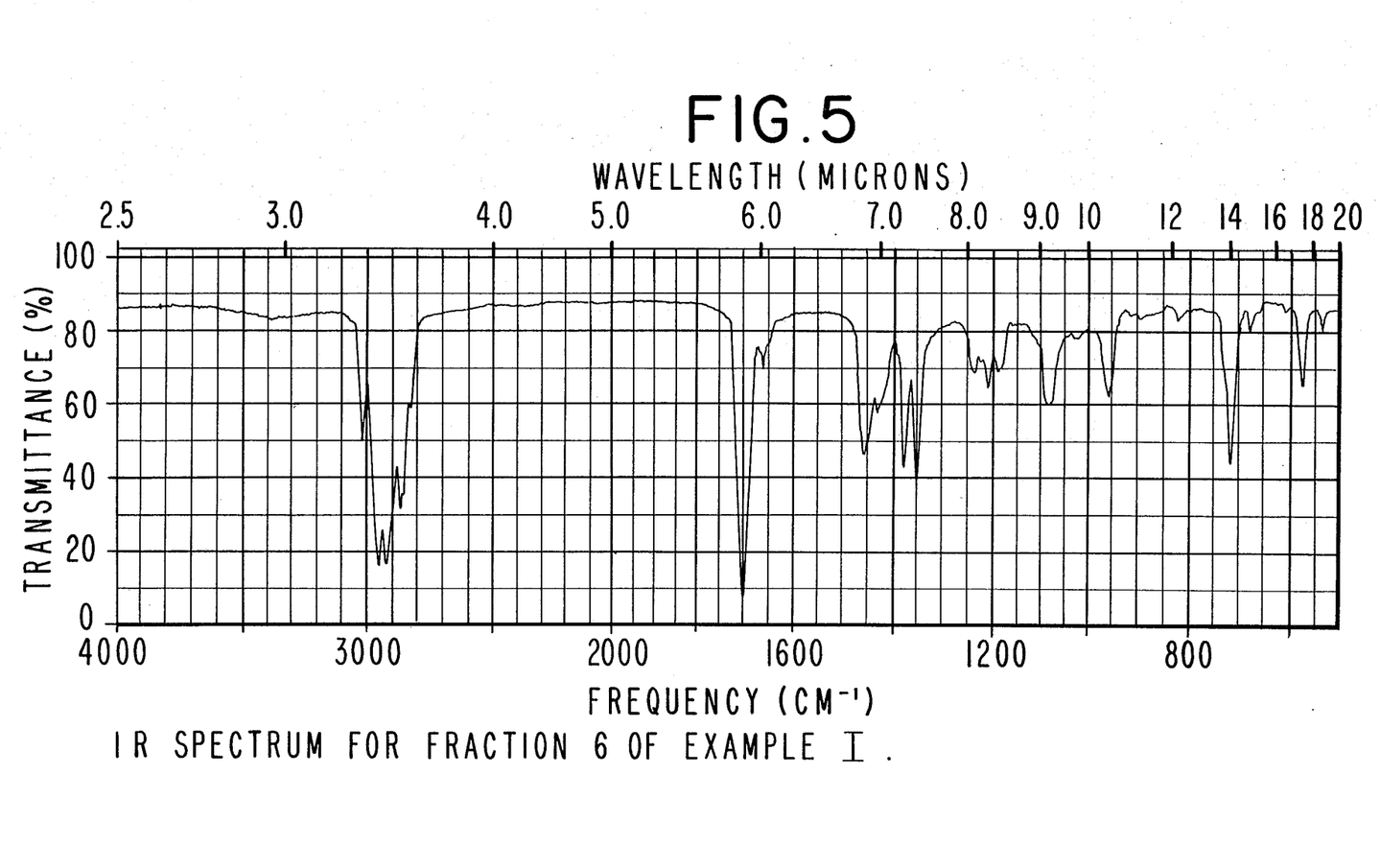
FIG. 5 is the infra-red spectrum for Fraction 6 of the distillation product of the reaction product of Example I containing the compound having the structure.

FIG. 5 is the infra-red spectrum for Fraction 6 of the foregoing distillation.

Fraction 6, has a green, violet, floral, woody and peppery and amber aroma profile from a perfumery standpoint.

From a smoking tobacco flavor standpoint, Fraction 6 has a fruity, hay-like and woody aroma and taste profile, both prior to and on smoking in both the main stream and the side stream.

EXAMPLE II

Patchouli/vetiver Formulation

The compound defined according to the structure:

(bulked fractions 6 and 7) is utilized in a perfumery formulation to form a patchouli/vetiver perfume formulation as follows:

| Ingredients | Parts by Weight |
|---|---|
| The compound having the structure:<br><br> | 479 |
| bulked fractions 6 and 7 produced according to Example I. | |
| Isobornyl acetate | 100 |
| Camphor | 10 |
| Terpineol | 25 |
| Fir balsam absolute (50% in diethyl phthalate) | 20 |
| Coumarin | 4 |
| Linalool | 30 |
| Anethol | 2 |
| Fenchyl alcohol | 10 |
| Lemon terpenes washed | 50 |
| Borneol | 5 |
| Galbanum oil | 5 |
| Turpentine Russian | 150 |
| Pine Oil | 50 |
| Eucalyptol | 50 |
| 2,2,6-trimethyl-1-cyclohexene-1-carboxaldehyde | 5 |
| Maltol 1% in diethyl phthalate | 5 |

The presence of the compound defined according to the structure:

blends to this vetiver formulation an intense patchouli character with green, violet, floral, woody, peppery and amber undertones. Accordingly the overall composition can be described as patchouli and vetiver with green, violet, floral, woody, peppery and amber undertones.

EXAMPLE III

Preparation of Cosmetic Powder Compositions

Cosmetic powder compositions are prepared by mixing in a ball mill, 100 grams of talcum powder (per composition) with 0.25 grams of the substance set forth in Table I below (per composition). Each of the cosmetic powder compositions has an excellent aroma as described in Table I below:

TABLE I

| Substance | Aroma Description |
|---|---|
| The compound defined according to the structure:<br><br>bulked fractions 6 and 7 prepared according to Example I. | A green, violet, floral, woody, peppery and amber aroma profile. |
| A perfume composition of Example II. | A green, violet, floral, woody, peppery and amber undertones. |

EXAMPLE IV

Perfumed Liquid Detergents

Concentrated liquid detergents (lysine salt of n-dodecylbenzene sulfonic acid as more specifically described in U.S. Pat. No. 3,948,818, issued on Apr. 6, 1976 incorporated by reference herein) with aroma nuances as set forth in Table I of Example III, are prepared containing 0.10%, 0.15%, 0.20%, 0.25%, 0.30% and 0.35% of the substance set forth in Table I of Example III. They are prepared by adding and homogeneously mixing the appropriate quantity of substance set forth in Table I of Example III in the liquid detergent. The detergents all possess excellent aromas as set forth in Table I of Example III, the intensity increasing with greater concentrations of substance as set forth in Table I of Example III.

EXAMPLE V

Preparation of Colognes and Handkerchief Perfumes

Compositions as set forth in Table I of Example III are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25%, and 30% (in 80%, 85%, 90% and 95% aqueous food grade ethanol solutions). Distinctive and definitive fragrances as set forth in Table I of Example III are imparted to the colognes and to the handkerchief perfumes at all levels indicated.

EXAMPLE VI

Preparation of Soap Compositions

One hundred grams of soap chips (per sample) (IVORY ®, produced by the Procter & Gamble Company of Cincinnati, Ohio), are each mixed with one gram samples of substances as set forth in Table I of Example III until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table I of Example III.

EXAMPLE VII

Preparation of Solid Detergent Compositions

Detergents are prepared using the following ingredients according to Example I of Canadian Pat. No. 1,007,948 (incorporated by reference herein):

| Ingredient | Percent by Weight |
| --- | --- |
| Neodol ® 45-11 (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table I of Example III. Each of the detergent samples has an excellent aroma as indicated in Table I of Example III.

EXAMPLE VIII

Utilizing the procedure of Example I at column 15 of U.S. Pat. No. 3,632,396 (the disclosure of which is incorporated herein by reference), nonwoven cloth substrates useful as drier-added fabric softening articles of manufacture are prepared wherein the substrate, the substrate coating, the outer coating and the perfuming material are as follows:
1. A water "dissolvable" paper ("Dissolvo Paper");
2. Adogen 448 (m.p. about 140° F.) as the substrate coating; and
3. An outer coating having the following formulation (m.p. about 150° F.):
57% $C_{20-22}$ HAPS
22% isopropyl alcohol
20% antistatic agent
1% of one of the substances as set forth in Table I of Example III.

Fabric softening compositions prepared according to Example I at column 15 of U.S. Pat. No. 3,632,396 having aroma characteristics as set forth in Table I of Example III, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table I of Example III is admixed in each case with the outer coating mixture, thereby providing a total aromatized outer coating weight ratio to substrate of about 0.5:1 by weight of the substrate. The aroma characteristics are imparted in a pleasant manner to the head space in a drier on operation thereof in each case using said drier-added fabric softener non-woven fabrics and these aroma characteristics are described in Table I of Example III, supra.

EXAMPLE IX

Hair Spray Formulations

The following hair spray formulation is prepared by first dissolving PVP/VA E-735 copolymer manufactured by the GAF Corporation of 140 West 51st Street, New York, N.Y. in 91.62 grams of 95% food grade ethanol. 8.0 grams of the polymer is dissolved in the alcohol. The following ingredients are added to the PVP/VA alcoholic solution:

| | |
| --- | --- |
| Dioctyl sebacate | 0.05 weight percent |
| Benzyl alcohol | 0.10 weight percent |
| Dow Corning 473 fluid (prepared by the Dow Corning Corporation) | 0.10 weight percent |
| Tween 20 surfactant (prepared by ICI America Corporation) | 0.03 weight percent |
| One of the perfumery substances as set forth in Table I of Example III, supra | 0.10 weight percent |

The perfuming substances as set forth in Table I of Example III add aroma characteristics as set forth in Table I of Example III which are rather intense and aesthetically pleasing to the users of the soft-feel, good-hold pump hair sprays.

EXAMPLE X

Conditioning Shampoos

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "Composition A".

Gafquat ®755N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation. This material is "Composition B".

The resulting Composition A and Composition B are then mixed in a 50:50 weight ratio of A:B and cooled to 45° C. and 0.3 weight percent of perfuming substance as set forth in Table I of Example III is added to the mixture. The resulting mixture is cooled to 40° C. and blending is carried out for an additional one hour in each case. At the end of this blending period, the resulting material has a pleasant fragrance as indicated in Table I of Example III.

EXAMPLE XI

Perfumed Polymer

Scented polyethylene pellets having a pronounced patchouli/vetiver aroma are prepared as follows:

75 Pounds of polyethylene of a melting point of about 220° F. were heated to about 230° F. in a container of the kind illustrated in FIGS. 1 and 2 of U.S. Pat. No. 3,505,432, the disclosure of which is incorporated by reference herein. 25 Pounds of the patchouli/vetiver formulation of Example II were then quickly added to the liquified polyethylene, the lid was put in place and the agitating means were actuated. The temperature was maintained at about 225° F. and the mixing was continued for about 5-15 minutes. The valve was then opened to allow flow of the molten polyethylene enriched with the patchouli/vetiver-containing material to exit through the orifices. The liquid falling through the orifices solidified almost instantaneously upon impact with the moving cooled conveyor. Solid polyethylene beads or pellets having a pronounced patchouli/vetiver scent were thus formed (green, violet, floral, woody, peppery and amber undertones). Analysis demonstrated that the pellets contained about 25% of the patchouli/vetiver formulation of Example II so that almost no losses of the scenting substance did occur. These pellets may be called master pellets.

50 Pounds of the patchouli/vetiver containing master pellets were then added to 1000 pounds of unscented polyethylene powder and the mass was heated to the liquid state in the equipment of U.S. Pat. No. 3,505,432. The liquid was molded into thin sheets or films. The thin sheets or films had a pronounced patchouli/vetiver aroma and were used in standard air freshening/scenting equipment.

EXAMPLE XII

Tobacco Formulation

A tobacco mixture is produced by admixing the following ingredients:

| Ingredients | Parts by Weight |
| --- | --- |
| Bright | 40.0 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.
The following flavor formulation is prepared:

| Ingredients | Parts by Weight |
| --- | --- |
| Ethyl butyrate | 0.05 |
| Ethyl valerate | 0.05 |
| Maltol | 2.00 |
| Cocoa extract | 26.00 |
| Coffee extract | 10.00 |
| Ethyl alcohol | 20.00 |
| Water | 41.90 |

The above-stated tobacco flavor formulation is applied at the rate of 1.0% to all of the cigarettes produced using the above tobacco formulation. Half of the cigarettes are then treated with 150 or 250 ppm of the compound defined according to the structure:

produced according to Example I. The control cigarettes not containing the compound having the structure:

and the experimental cigarettes which contain the compound having the structure:

are evaluated by paired comparison and the results are as follows:

The experimental cigarettes are found to have more body in tobacco smoke flavor and a fuller body sensation. The tobacco-like notes are enhanced and the flavor of the tobacco on smoking is more aromatic with fruity, hay-like and woody aroma and taste nuances.

The tobacco smoke flavor of the experimental cigarettes prior to smoking, has sweet, fruity, hay, spicey and woody notes. All cigarettes are evaluated for smoke flavor with a 20 mm cellulose acetate filter.

When the compound having the structure:

is added to the filter rather than to the tobacco at either 50 ppm or 100 ppm, an interesting and pleasant fruity, hay-like and woody aroma is obtained prior to and on smoking the cigarettes.

What is claimed is:

1. A process for augmenting or enhancing the aroma or taste of a consumable material selected from the group consisting of perfume compositions, colognes, perfumed articles, smoking tobacco compositions and smoking tobacco articles comprising the step of adding to said consumable material an aroma or taste augmenting or enhancing quantity of the compound defined according to the structure:

2. The process of claim 1 wherein the consumable material is a perfume composition or cologne.

3. The process of claim 1 wherein the consumable material is a perfumed article and the perfumed article is a solid or liquid anionic, cationic, nonionic or zwitterionic detergent.

4. The process of claim 1 wherein the consumable material is a perfumed article and the perfumed article is a perfumed polymer.

5. The process of claim 1 wherein the consumable material is a smoking tobacco or smoking tobacco article.

6. The process of claim 1 wherein the consumable material is a perfumed article and the perfumed article is a fabric softener composition or drier-added fabric softener article.

7. The process of claim 1 wherein the consumable material is a cosmetic powder.